United States Patent [19]

Aoki et al.

[11] 4,091,109
[45] May 23, 1978

[54] DIPHENYLETHER DERIVATIVES AND USE THEREOF AS AN ACARICIDE

[75] Inventors: Yukio Aoki, Omiya; Shizuo Wakita, Ageo; Shoichi Kato, Ageo; Iwao Tejima, Ageo; Shuichi Ishida, Omiya, all of Japan

[73] Assignee: Nippon Kayaku Kabushiki Kaisha, Tokyo, Japan

[21] Appl. No.: 697,532

[22] Filed: Jun. 18, 1976

[51] Int. Cl.² .................. A01N 9/12; A01N 9/20; C07C 121/52; C07C 149/32
[52] U.S. Cl. .................. 424/304; 260/465 F; 260/607 AR; 260/609 F; 424/337
[58] Field of Search .................. 424/304, 337; 260/465 F, 609 F, 607 AR

[56] References Cited

U.S. PATENT DOCUMENTS

| | | | |
|---|---|---|---|
| 3,647,888 | 3/1972 | Rohr et al. | 424/337 |
| 3,766,238 | 10/1973 | Rohr | 424/304 |
| 3,798,276 | 3/1974 | Bayer | 260/609 F |
| 3,813,444 | 5/1974 | Abe et al. | 260/607 AR |
| 3,821,312 | 6/1974 | Abe et al. | 260/609 F |
| 3,857,954 | 12/1974 | Aoki et al. | 424/337 |
| 3,928,408 | 12/1975 | Hammann et al. | 260/465 F |
| 3,957,865 | 5/1976 | Rohe et al. | 260/609 F X |
| 3,998,972 | 12/1976 | Farooq et al. | 424/337 |

OTHER PUBLICATIONS

Degering; An Outline of Organic Nitrogen Compounds, (1945) p. 518.

Primary Examiner—Allen J. Robinson
Attorney, Agent, or Firm—Russell & Nields

[57] ABSTRACT

Compounds of the formula

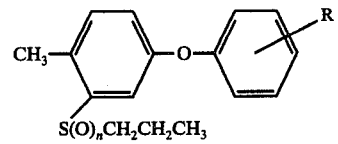

wherein R represents CN, SCH$_3$, Cl, Br or CF$_3$ and $n$ represents 0 or 1, have very excellent acaricidal activity.

3 Claims, No Drawings

DIPHENYLETHER DERIVATIVES AND USE THEREOF AS AN ACARICIDE

BACKGROUND OF THE INVENTION

It is shown in West German Offenlegungsschrift No. 2,307,248 that derivatives of 4-nitro diphenylether have an excellent acaricidal activity. The derivatives of diphenylether of the present invention have no nitro substituent on the phenyl ring and yet have an acaricidal activity superior to that of said derivatives of 4-nitro diphenyl ether. Furthermore the compounds of the present invention have an excellent residual efficacy.

DETAILED DESCRIPTION OF THE INVENTION

The present invention relates to new derivatives of diphenylether represented by the formula

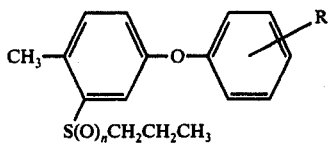

wherein R is CN, $SCH_3$, Cl, Br or $CF_3$ and $n$ is 0 or 1, an acaricidal composition comprising 0.5–90% by weight of the new derivatives of diphenylether and 99.5–10% by weight of adjuvants and a method for exterminating acarids comprising applying to acarids and their eggs an effective amount of the new derivatives of diphenylether.

The new derivative of diphenylether of the present invention is prepared by condensing a compound of the formula

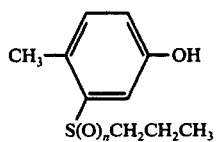

wherein $n$ is 0 or 1 or an alkali metal salts thereof with a compound of the formula

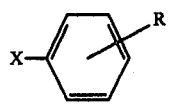

wherein X is an halogen such as chlorine or bromine, R is the same meaning as defined hereinbefore in an inert organic solvents.

When the starting materials are not the alkalimetal salts of the compound of the formula [II] the condensation is conducted in the presence of an alkali metal hydroxide such as sodium hydroxide or potassium hydroxide or metal powder such as Cu powder.

The present compounds of the formula

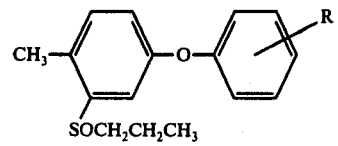

are also prepared by oxidizing the compound of the formula

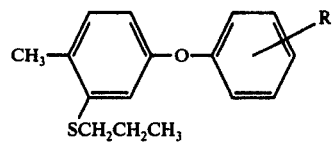

with an oxidizing agent such as hydrogen peroxide.

The preferred compounds are compounds of the formula [I] wherein R is p-CN, p-$SCH_3$, p-Cl, p-Br, p-$CF_3$ or m-$CF_3$ and $n$ is 0 or 1.

The method for the preparation is illustrated by the following Preparation Examples.

PREPARATION EXAMPLE 1

4-Methyl-3-n-propylthiophenyl 4-methylthiophenyl ether.

4-Methyl-3-(n-propylthio)phenol (4.0 g, 0.02 mole) and 85.5% potassium hydroxide (1.4 g, 0.02 mole) were dissolved in N,N-dimethylacetamide (40 ml) above 90° C. 4-Bromomethylthiobenzene (4.0 g, 0.02 mole) and Cu powder (0.5 g, 0.008 mole) were added to this solution below 90° C and the mixture was stirred at 120°–160° C for 14 hr. After cooling, the reaction mixture was poured into water (100 ml) and extracted twice with benzene. The combined organic layers were washed with 5% sodium hydroxide solution, 5% hydrochloric acid solution, and water, then dried over sodium sulfate. The solvent was removed, and the residue was distilled under reduced pressure. The yield of 4-methyl-3-n-propylthiophenyl 4-methylthiophenyl ether was 4.1 g (61.5%), colorless oil, bp 188°–190° C/2 mmHg. Anal. Found: C, 67.12; H, 6.59. Calcd. for $C_{17}H_{20}OS_2$: C, 67.06; H, 6.62%

PREPARATION EXAMPLE 2

4-Methyl-3-n-propylsulfinylphenyl 3-trifluoromethylphenyl ether (A) Preparation of 4-methyl-3-n-propylthiophenyl 3-tri fluoromethylphenyl ether 4-Methyl-3-(n-propylthio)phenol (8.4 g, 0.05 mole) and 85.5% potassium hydroxide (3.3 g, 0.05 mole) were dissolved in N,N-dimethylacetamide (50 ml) above 90° C. 3-Bromotrifluoromethylbenzene (11.2 g, 0.05 mole) and Cu powder (0.5 g, 0.008 mole) were added to this solution below 90° C and the mixture was stirred at 110°–160° C for 14 hr. After cooling, the reaction mixture was poured into water (150 ml) and extracted twice benzene. The combined organic layers were washed with 5% sodium hydroxide solution, 5% hydrochloric acid solution, and water, then dried over sodium fulfate. The solvent was removed, and the residue was purified by column chromatography on silica gel using n-hexane benzene (2 : 1). The yield of 4-methyl-3-n-propylthiophenyl 3-trifluoromethylphenyl ether was 8.9 g (54.8%), colorless oil, $n_D^{25}$ 1.5319. Anal. Found: C, 62.61; H, 5.33. Calcd. for $C_{17}H_{17}F_3OS$ : C, 62.56; H, 5.25%.

(B) Preparation of 4-methyl-3-n-propylsulfinylphenyl 3-trifluoromethylphenyl ether Thirty-five percent hydrogen peroxide solution (1.6 g, 0.016 mole) was added at 8°–10° C to a mixture of 4-methyl-3-n-propylthiophenyl 3-trifluoromethylphenyl ether (3.8 g, 0.012 mole) and glacial acetic acid (30 ml). After 5 hr at room temperature, the reaction mixture was poured into water (100 ml) and extracted three times with benzene. The combined organic layers were washed with 5% sodium carbonate solution, then water and dried over sodium sulfate. Evaporation of the solvent gave 3.8 g (92.5%) of 4-methyl-3-n-propylsulfinylphenyl 3-trifluoromethylphenyl ether, colorless oil, $n_D^{25}$ 1.5350. Anal. Found: C, 59.50; H, 5.11. Calcd. for $C_{17}H_{17}F_3O_2S$ : C, 59.64; H, 5.01%.

The representative compounds are shown in Table 1.

Table 1.

The formula

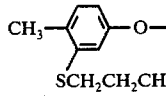

S(O)$_n$CH$_2$CH$_2$CH$_3$

| Compound No. | R | n | m.p., b.p. (° C) or $n_D^{25}$ | Appearance |
|---|---|---|---|---|
| 1 | p-CN | 0 | m.p. 52° C | White crystals |
| 2 | p-Cl | 0 | $n_D^{25}$ 1.5950 | Colorless oil |
| 3 | p-SCH$_3$ | 0 | b.p.188–190° C/2mmHg | " |
| 4 | p-Br | 0 | $n_D^{25}$ 1.6081 | " |
| 5 | p-CF$_3$ | 0 | $n_D^{25}$ 1.5415 | " |
| 6 | m-CF$_3$ | 1 | $n_D^{25}$ 1.5350 | " |
| 7 | p-Cl | 1 | $n_D^{25}$ 1.5920 | " |

The compound of the present invention can be used as an acaricide singly or in combination with one or more suitable adjuvants in the form of emulsion, wettable powder, dust or granules. The adjuvants include a carrier and a supplementary material which is usually employed in agricultural chemicals. The carrier may be solid, liquid or gaseous. That is to say, the solid carriers are, for example, clay, talc, bentonite, white carbon, kaolin, diatomaceousearth and silica. The liquid carriers are, for example, water, benzene, kerosene, alcohols, acetone, xylene, methylnapthalene, cyclohexane, animal and plant oils, aliphatic acids and esters of aliphatic acid. And the gaseous carriers are air, nitrogen, carbon dioxide, Freon and the like.

The supplementary material includes, for example, a spreader, an emulsifier, a sticking agent, a wetting or a surface active agent, namely polyoxyethylene alkylallyl ether, polyvinyl alcohol, polyoxyethylene sorbitan monooleate, alkyldimethyl benzyl ammonium chloride, alkylbenzensulfonate, ligninsulfonate, an ester of higher alcohol of sulfuric acid, etc.

The acaricidal composition of the present invention comprise 0.5–90%, preferably, 1–50% by weight of the compound of the formula [I] and 99.5–10%, preferably 99–50% by weight of the adjuvants.

When the compound of the present invention is used for an acaricide in the form of an emulsion or a wettable powder, the concentration of the compound in the acaricide is within a range of 5–70%, preferably 10–50% by weight, and the acaricide is diluted with water within a range of 0.1–0.01% by weight before sprinkling, and the acaricide diluted is sprinkled in an amount of 100–1000 liter per 10 ares.

When used in the form of powder or granule, the concentration is within a range of 0.5–5% by weight and the acaricide is used within a range of 1–5 kg per 10 ares.

The compounds of the present invention can be used in admixture with other agricultural fungicides, insecticides, plant growth regulators or liquid fertilizers.

The excellent acaricidal activity of the compound of the present invention is illustrated by the following Experimental Examples.

EXPERIMENTAL EXAMPLE 1

A leaf of summer orange which was cut 2 cm square was put on the agar gel which was poured into the petri dish (9 cm in diameter). The leaf was enclosed by an adhesive substance to prevent the escape of mites and then 20 female adults of citrus red mites which were catched in a farm of Ageo-shi Saitama-ken, Japan were inoculated per leaf. One day after the inoculation, dead and feeble mites were removed from the leaf and then 7 ml of 25 ppm solution of a acaricidal compound were sprayed per dish. After spraying, the dish was kept in the constant temperature room controlled at 25° C for 48 hours and then the death or survivor of the mites were examined. The results were shown in Table 2.

Table 2.

| Compound | Mortality (%) |
|---|---|
| 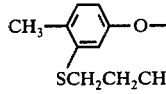 (Compound No.1) | 62.5 |
| 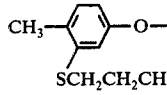 (Compound No.2) | 80.0 |
| 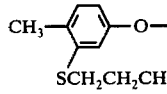 (Compound No.3) | 100.0 |
| 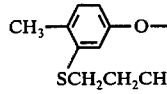 (Compound No.4) | 86.6 |
| CH$_3$—⟨⟩—O—⟨⟩—NO$_2$<br>SCH$_2$CH$_2$CH$_3$ | 16.2 |

(The closest compound of west German Offenlegungs-schrift 2307248)

EXPERIMENTAL EXAMPLE 2

Mite-killing tests of the Experimental Example 1 were repeated except that the concentration of an acaricidal compound in the solution was changed to 12.5 ppm. The results were shown in Table 3.

Table 3.

| Compound | Mortality (%) |
|---|---|
| 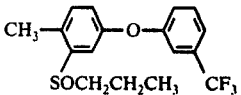 (Compound No.6) | 100 |
| 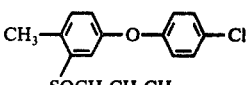 (Compound No.7) | 85.7 |
| 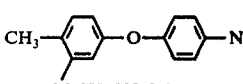 (The closest compound of West German Offenlegungs-schrift 2307248) | 38.1 |

EXPERIMENTAL EXAMPLE 3

Each of 2 seed leaves of young kidney-bean which were cultivated in porous pots was cut into the pieces of about 2 cm square. The leaves were immersed in a 0.01% (by weight) solution of an acaricidal compound. After the leaves were left for 1 day in a room as-is, 15 female imagos of two spotted spider mites were inoculated per leaf. Two days after inoculation, the death or survival of the mites was examined. Test were conducted 2 replicates.

The results are shown in Table 4.

Table 4.

| Compound | Mortality (%) |
|---|---|
| 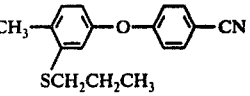 (Compound No.1) | 100 |
| 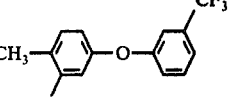 (Compound No.6) | 78.3 |
| 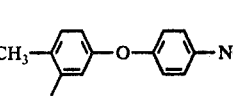 (A compound of West German Offenlegungs-schrift 2307248) | 33.3 |

The results show that the compounds of the present invention show good residual efficacy.

The acaricidal compositions of the present invention are concretely illustrated by the following composition Examples.

COMPOSITION EXAMPLE 1 (EMULSION)

| | |
|---|---|
| Compound No.3 | 20 parts by weight |
| Xylene | 65 parts by weight |
| The mixture of calcium alkylbenzenesulfonate and the condensation products of alkylphenol and ethyleneoxide | 15 parts by weight |

The components mentioned above were mixed and pulverized into fine powder.

When, used, the fine powder was diluted with water and the resultant mixture was sprinkled.

COMPOSITION EXAMPLE 3 (POWDER)

| | |
|---|---|
| Compound No.8 | 3 parts by weight |
| Clay | 48 parts by weight |
| Talc | 48 parts by weight |
| Synthetic hydrated silicic acid | 1 part by weight |

The components mentioned above were mixed and pulverized into powder. When used, the powder was scattered.

We claim:

1. A compound represented by the formula

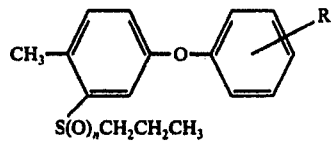

wherein R represents CN, SCH$_3$, Cl, Br or CF$_3$ and $n$ represents 0 or 1.

2. An acaricidal composition comprising 0.5–90% by weight of a compound of the formula

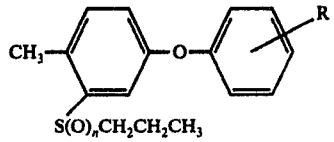

wherein R represents CN, SCH$_3$, Cl, Br or CF$_3$ and $n$ represents 0 or 1 and 99.5–10% by weight of adjuvants.

3. A method for exterminating acarids comprising applying to acarids and their eggs an acaricidally effective amount of a compound of the formula

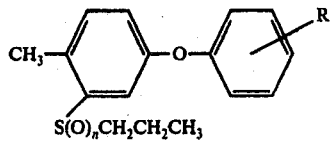

wherein R represents CN, SCH$_3$, Cl, Br or CF$_3$ and $n$ represents 0 or 1.

* * * * *